(12) United States Patent
Cheng et al.

(10) Patent No.: US 8,129,555 B2
(45) Date of Patent: Mar. 6, 2012

(54) PRECURSORS FOR DEPOSITING SILICON-CONTAINING FILMS AND METHODS FOR MAKING AND USING SAME

(75) Inventors: Hansong Cheng, Allentown, PA (US); Manchao Xiao, San Diego, CA (US); Gauri Sankar Lal, Whitehall, PA (US); Thomas Richard Gaffney, Carlsbad, CA (US); Chenggang Zhou, Wuhan (CN); Jinping Wu, Wuhan (CN)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 12/190,125

(22) Filed: Aug. 12, 2008

(65) Prior Publication Data

US 2010/0041243 A1 Feb. 18, 2010

(51) Int. Cl.
*C07F 7/10* (2006.01)
*H01L 21/31* (2006.01)
(52) U.S. Cl. .......... 556/410; 548/406; 546/14; 438/778; 257/E21.269
(58) Field of Classification Search .................. 556/410; 548/406; 546/14; 438/778; 257/E21.269
See application file for complete search history.

(56) References Cited

U.S. PATENT DOCUMENTS 5,234,869 A 8/1993 Mikata et al.
(Continued)

FOREIGN PATENT DOCUMENTS

JP 6132284 A 5/1994

OTHER PUBLICATIONS

Gilman et al., 82 JACS, 3319-20 (1960).*

(Continued)

*Primary Examiner* — Porfirio Nazario Gonzalez
(74) *Attorney, Agent, or Firm* — Rosaleen P. Morris-Oskanian

(57) ABSTRACT

Aminosilane precursors for depositing silicon-containing films, and methods for depositing silicon-containing films from these aminosilane precursors, are described herein. In one embodiment, there is provided an aminosilane precursor for depositing silicon-containing film comprising the following formula (I):

$$(R^1R^2N)_n SiR^3_{4-n} \qquad (I)$$

wherein substituents $R^1$ and $R^2$ are each independently chosen from an alkyl group comprising from 1 to 20 carbon atoms and an aryl group comprising from 6 to 30 carbon atoms, at least one of substituents $R^1$ and $R^2$ comprises at least one electron withdrawing substituent chosen from F, Cl, Br, I, CN, $NO_2$, $PO(OR)_2$, OR, SO, $SO_2$, $SO_2R$ and wherein R in the at least one electron withdrawing substituent is chosen from an alkyl group or an aryl group, $R^3$ is chosen from H, an alkyl group, or an aryl group, and n is a number ranging from 1 to 4.

21 Claims, 2 Drawing Sheets

U.S. PATENT DOCUMENTS

| | | | |
|---|---|---|---|
| 5,429,673 | A | 7/1995 | Peterson et al. |
| 5,874,368 | A | 2/1999 | Laxman et al. |
| 6,869,638 | B2 | 3/2005 | Baum et al. |
| 7,875,312 | B2 | 1/2011 | Thridandam et al. |
| 2004/0146644 | A1* | 7/2004 | Xiao et al. ............... 427/255.28 |
| 2006/0178019 | A1 | 8/2006 | Senzaki et al. |
| 2006/0182885 | A1* | 8/2006 | Lei et al. .................... 427/248.1 |
| 2006/0258173 | A1* | 11/2006 | Xiao et al. .................... 438/780 |

OTHER PUBLICATIONS

Ge McGuire, Semiconductor materials and process technology handbook: for very large . . . , Mat. sci. and process tech. series, Noyes Pub., 1988, pp. 289-301.

Stanley Wolf, Silicon processing for the VLSI Era, 1990, 2, pp. 20-22 and 327-331.

Tetsuji Sorita et al, Mass spectrometric and kinetic study of low-pressure chemical vapor deposition . . . , J. Elec. Soc., 1994, 141, pp. 3505-3511.

B.A. Scott et al, Preparation of silicon nitride with good interface properties by homogeneous chemical vapour deposition, Chemtronics, Dec. 1989, 4, pp. 230-234.

J.M. Grow et al, Growth kinetics and characterization of low pressure chemically vapor deposited . . . , Mat. Letters 23, 1995, pp. 187-193.

Arthur K. Hochberg et al, Diethylsilane as a silicon for the deposition of silicon nitride and silicon . . . , Mat. Res. Soc. Symp. Proc., 1991, vol. 204, pp. 509-514.

Roy G. Gordon et al, Silicon dimethylamido complexes and ammonia as precursors for the atmospheric . . . , Chem. Mater. 1990, 2, pp. 480-482.

Wen-Chang Yeh et al, Low-temperature chemical-vapor-deposition of silicon-nitride film from . . . , Jpn. J. Appl. Phys. vol. 35, 1996, Part 1, No. 2B, pp. 1509-1512.

Hsin-Tien Chiu, Chemical Vapor Deposition, Kirk-Othmer Encyclopedia of Chem. Tech., 2003, vol. 5, pp. 803-813.

Hiroto Yoshida, Aminosilylation of arynes with aminosilanes: synthesis of 2-silylaniline derivatives, Chem. Commun., 2005, 3454-3456.

H. Kohler, et al, Chemistry of the Dicyanamide and Tricyanomethanide Ion XII. Organosilicon Dicyanamides and Tricyanomethanides, J. Organometal. Chem, 1968, 103-107.

I. Ruppert, Silylcarbodiimides by Silylation of Organylcyanamides, Tetrahedron Letters No. 23, 1997, 1987-1990.

* cited by examiner

PRECURSORS FOR DEPOSITING SILICON-CONTAINING FILMS AND METHODS FOR MAKING AND USING SAME

BACKGROUND OF THE INVENTION

Precursors, particularly aminosilane precursors that can be used for the deposition of silicon-containing films, including but not limited to, silicon nitride, silicon oxide, silicon carbonitride, and silicon oxynitride films are described herein. In one aspect, described herein is a method for making aminosilane precursors. In yet another aspect, described herein is the use of the aminosilane precursors for depositing silicon-containing dielectric films in the fabrication of integrated circuit devices. In these or other aspects, the aminosilane precursors may be used for a variety of deposition processes, including but not limited to, atomic layer deposition ("ALD"), chemical vapor deposition ("CVD"), plasma enhanced chemical vapor deposition ("PECVD"), low pressure chemical vapor deposition ("LPCVD"), and atmospheric pressure chemical vapor deposition.

Silicon-containing dielectric films play an important role in the fabrication of semiconductor devices or integrated circuits. In the fabrication of semiconductor devices, a thin passive layer of a chemically inert dielectric material such as, for example, silicon nitride may be essential. One or more thin layers of silicon nitride may act within the device as, for example, a diffusion mask or barrier, an oxidation barrier, a gate insulator for trench isolation, a capacitor dielectric, an intermetallic material with high dielectric breakdown voltage, and/or a passivation layer. Silicon nitride film may also be used as sidewall spacers in metal oxide semiconductor alone, or in combination with silicon oxide and/or silicon oxynitride dielectrics in devices such as Groups IV and 11-V transistors. Other applications for silicon-containing dielectrics such as silicon nitride films are found, for example, in the reference *Semiconductor and Process Technology Handbook*, edited by Gary E. McGuire, Noyes Publication, New Jersey, (1988), pp. 289-301.

Several classes of silicon-containing compounds can be used as precursors for silicon-containing films such as silicon nitride films. Examples of these silicon-containing compounds suitable for use as precursors include silanes, chlorosilanes, polysilazanes, aminosilanes, and azidosilanes. Inert carrier gas or diluents such as, but not limited, helium, hydrogen, nitrogen, etc., are also used.

Low pressure chemical vapor deposition (LPCVD) processes are one of the more widely accepted methods used by semiconductor industry for the deposition of silicon-containing films. Low pressure chemical vapor deposition (LPCVD) using ammonia may require deposition temperatures of greater than 750° C. to obtain reasonable growth rates and uniformities. Higher deposition temperatures are typically employed to provide improved film properties. One of the more common industry methods to grow silicon nitride or other silicon-containing films is through low pressure chemical vapor deposition in a hot wall reactor at temperatures >750° C. using the precursors silane, dichlorosilane, and/or ammonia. However, there are several drawbacks using this method. For example, certain precursors, such as silane and dichlorosilane, are pyrophoric. This may present problems in handling and usage. Also, films deposited from silane and dichlorosilane may contain certain impurities. For example, films deposited using dichlorosilane may contain certain impurities, such as chlorine and ammonium chloride, which are formed as byproducts during the deposition process. Films deposited using silane may contain hydrogen.

Japanese Patent 6-132284 describes the formation of silicon nitride films using organosilanes having a general formula $(R_1R_2N)_nSiH_{4-n}$ by either a plasma enhanced chemical vapor deposition or thermal chemical vapor deposition in the presence of ammonia or nitrogen. These organosilane precursors were tertiary amines and did not contain NH bonding. The deposition experiments were carried out in a single wafer reactor at 400° C. at pressures ranging from 80-100 Torr.

The reference Sorita et al., *Mass Spectrometric and Kinetic Study of Low-Pressure Chemical Vapor Deposition of $Si_3N_4$ Thin Films From $SiH_2Cl_2$ and $NH_3$*, J. Electro. Chem. Soc., Vol. 141, No. 12, (1994), pp 3505-3511, describes the deposition of silicon nitride using dichlorosilane and ammonia in a LPCVD process. The major products in this process are aminochlorosilane, silicon nitride and ammonium chloride. As previously mentioned, formation of ammonium chloride may be a major drawback of using Si—Cl containing precursors. The formation of ammonium chloride may lead to, inter alia, particle formation and deposition of ammonium chloride at the back-end of the tube, in the plumbing lines, and the pumping system. Processes which contain chlorine in the precursors may also result in $NH_4Cl$ formation. These processes may require frequent cleaning and result in large down time of the reactors.

The reference B. A. Scott et al., *Preparation of Silicon Nitride with Good Interface Properties by Homogeneous Chemical Vapour Deposition*, Chemtronics, 1989, Vol. 4, Dec., pp. 230-34, describes the deposition of silicon nitride using silane and ammonia by a homogenous CVD process at gas temperatures ranging from 500-800° C. while maintaining the substrate temperature at 200-500° C. As previously mentioned, the use of silane as a precursor may introduce hydrogen impurities into the film.

The reference J. M. Grow et al., *Growth Kinetics and Characterization of Low Pressure Chemically Vapor Deposited $Si_3N_4$ Films from $(C_4H_9)_2SiH_2$ and $NH_3$*, Materials Letters, 23, (1995), pp. 187-193, describes the deposition of silicon nitride using ditertiarybutylsilane and ammonia by a LPCVD process using temperatures ranging from 600-700° C. The deposited silicon nitride films were contaminated with approximately 10 atomic weight percent of carbon impurities.

The reference W-C. Yeh, R. Ishihara, S. Moishita, and M. Matsumura, Japan. J. Appl. Phys., 35, (1996) pp. 1509-1512, describes a low temperature deposition of a silicon-nitrogen film using hexachlorodisilane and hydrazine near 350° C. The films are unstable in air and slowly converted to a silicon-oxygen film.

The reference A. K. Hochberg and D. L. O'Meara, *Diethylsilane as a Silicon Source for the Deposition of Silicon Nitride and Silicon Oxynitride Films By LPCVD*, Mat. Res. Soc. Symp. Proc,. Vol. 204, (1991), pp. 509-514, discloses the formation of silicon nitride and silicon oxynitride films using diethylsilane with ammonia and nitric oxide by LPCVD. The deposition is carried out in a temperature range of 650° C. to 700° C. The deposition is limited generally to a temperature of 650° C. as the deposition rate drops to below 4 Angstroms/minute at lower temperatures. In the LPCVD process, precursors which contain direct Si—C carbon bonds result in carbon contamination in the films. Carbon free deposition requires greater than 5:1 $NH_3$ to precursor ratios. At lower ammonia concentrations, the films were found to contain carbon. Diethylsilane and ammonia processes typically require covered boats or temperature ramping to improve uniformities across the wafers.

U.S. Pat. No. 5,234,869 ("the '869 patent") discloses the formation of a silicon nitride film by LPCVD using Si(N (CH₃)₂)₄ and ammonia as reactant gases at 700° C. and a pressure of 0.5 Torr. Other reactants selected from the group consisting of SiH(N(CH₃)₂)₃, SiH₂(N(CH₃)₂)₂, and SiH₃(N(CH₃)₂) in combination with ammonia or nitrogen were also suggested as reactants. The '869 patent also discloses decreasing the deposition temperature to 300° C. through the use of a plasma produced from a gas or exciting a gas by radiating it with an ultra-violet beam.

The reference R. G. Gordon and D. M. Hoffman, *Silicon Dimethylamido Complexes and Ammonia as Precursors for the Atmospheric Pressure Chemical Vapor Deposition of Silicon Nitride Thin Films*, Chem. Mater., Vol. 2, (1990), pp 480-482 disclose other attempts to reduce the amount of carbon in the silicon nitride film involved aminosilanes, such as tetrakis (dimethylamino) silane. The reference discloses the deposition of silicon nitride films via APCVD using the precursor tetrakis(dimethylamido)silane Si(NMe₂)₄ and ammonia at a deposition temperature range of 600-750° C. The reference also teaches that film depositions using the Si(NMe$_n$)$_{4-n}$ without ammonia at a deposition temperature of 750° C. resulted in films that were obtained at slower growth rates and with large amounts of carbon (22-30%) and oxygen (15-17%) contamination.

U.S. Pat. No. 5,874,368 ("the '368 patent") describes the use of bis(tertiarybutylamino)silane (t-C₄H₉NH)₂SiH₂) and ammonia to deposit a silicon nitride film using a LPCVD process at a temperature range of 500° to 800° C.

Precursors that are used in depositing silicon nitride films such as BTBAS and chlorosilanes generally deposit the films at temperatures greater than 550° C. The trend of miniaturization of semiconductor devices and low thermal budget requires lower process temperature and higher deposition rate. The temperature, at which the silicon nitride film is deposited, should decrease in order to prevent ion diffusion in the lattice, particularly for those substrates comprising metallization layers and on many Group III-V and II-VI devices. Presently, none of the currently available silicon nitride precursors are chemically active enough to allow film deposition to occur at temperatures lower than 550° C. via CVD or ALD. Accordingly, there is a need in the art to provide precursors for the deposition of silicon nitride or other silicon-containing films that allow are sufficiently chemically reactive to allow deposition via CVD, ALD or other processes at temperatures of 550° C. or below.

BRIEF SUMMARY OF THE INVENTION

Described herein are aminosilane precursors that are used for depositing silicon-containing films, methods for making the aminosilane precursors, and methods for using the aminosilane precursors, for example, in the deposition of a silicon-containing film. In one embodiment, there is provided an aminosilane precursor for depositing silicon-containing film comprising the following formula (I):

$$(R^1R^2N)_n SiR^3_{4-n} \tag{I}$$

wherein substituents $R^1$ and $R^2$ are each independently chosen from an alkyl group comprising from 1 to 20 carbon atoms and an aryl group comprising from 6 to 30 carbon atoms, wherein at least one of substituents $R^1$ and $R^2$ comprises at least one electron withdrawing substituent chosen from F, Cl, Br, I, CN, NO₂, PO(OR)₂, OR, RCOO, SO, SO₂, SO₂R and wherein R in the at least one electron withdrawing substituent is chosen from an alkyl group or an aryl group, $R^3$ is chosen from a H atom, an alkyl group comprising from 1 to 20 carbon atoms, or an aryl group comprising from 6 to 12 carbon atoms, and n is a number ranging from 1 to 4.

In yet another embodiment, there is provided a process for depositing a silicon-containing film on a substrate via chemical vapor deposition comprising: providing the substrate in a process chamber; and introducing an aminosilane precursor into the process chamber at a temperature and a pressure sufficient to react and deposit the silicon-containing film on the substrate wherein the aminosilane precursors comprises the following formula (I):

wherein substituents $R^1$ and $R^2$ are each independently chosen from an alkyl group comprising from 1 to 20 carbon atoms and an aryl group comprising from 6 to 30 carbon atoms, wherein at least one of substituents $R^1$ and $R^2$ comprises at least one electron withdrawing substituent chosen from F, Cl, Br, I, CN, NO₂, PO(OR)₂, OR, RCOO, SO, SO₂, SO₂R and wherein R in the at least one electron withdrawing substituent is chosen from an alkyl group or an aryl group, $R^3$ is chosen from a H atom, an alkyl group comprising from 1 to 20 carbon atoms, or an aryl group comprising from 6 to 12 carbon atoms, and n is a number ranging from 1 to 4.

In a further embodiment, there is provided an aminosilane precursor for depositing silicon-containing film comprising the following formula (II):

wherein A is at least one group chosen from the following amino groups (a) through (i), $R^4$ is chosen from hydrogen, an alkyl group comprising from 1 to 20 carbon atoms, or an aryl group comprising from 6 to 12 carbon atoms, and n is a number ranging from 1 to 4

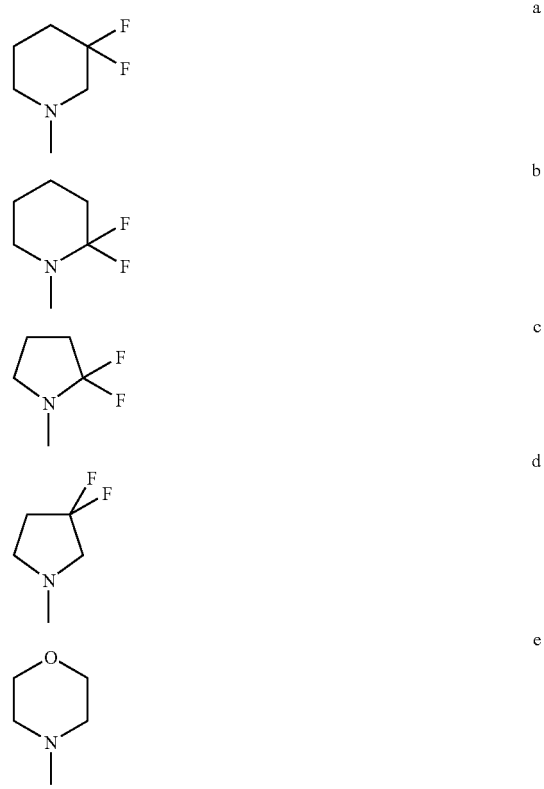

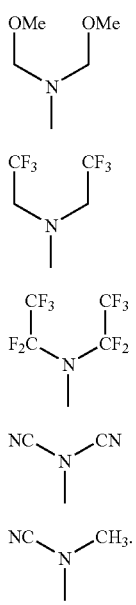

f g h i j

DETAILED DESCRIPTION OF THE INVENTION

Figure 1:
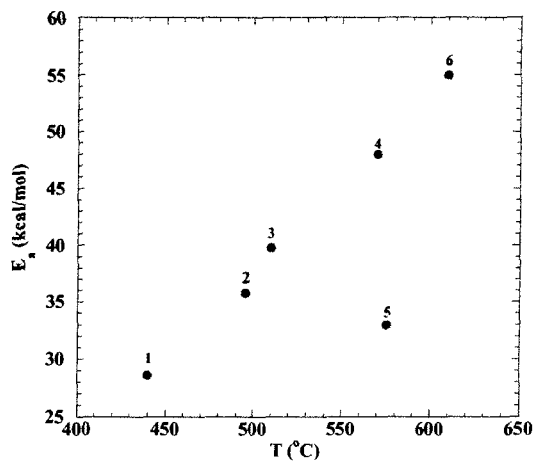
FIG. 1 provides a graphical representation of the correlation of experimentally measured deposition temperatures and the activation barrier levels for certain aminosilane precursors 1 through 6 described herein.

Disclosed herein are aminosilanes that can be used, for example, for the chemical vapor deposition of silicon nitride or other silicon and/or nitrogen containing films. These aminosilane precursors satisfy at least one of the needs in the art by providing precursors that may allow the deposition of silicon-containing films such as silicon nitride films at temperatures 550° C. or below. The aminosilane precursors described herein contain at least one electron withdrawing substituent. It is believed that the presence of the at least one electron withdrawing substituent within the precursor may cause the reaction energy, activation energy, or both for the deposition of the aminosilane precursor to decrease. In one particular embodiment, the reaction energy is defined herein in Equation (2). In this or other embodiments, the correlation between reaction energy and activation energy is provided in FIG. 3. It is believed that the decrease in reaction energy, activation energy, or both may allow the precursors described herein to be more chemically reactive relative to similar aminosilane precursors that do not contain the at least one electron withdrawing substituent. As a result of the more favorable energetics, the aminosilane precursors can be used to deposit silicon-containing films such as silicon nitride films at lower deposition temperatures (e.g., 550° C. or less).

In one embodiment, there are provided aminosilanes having the general formula (I):

$$(R^1R^2N)_n SiR^3_{4-n} \tag{I}$$

In formula (I), substituents $R^1$ and $R^2$ are each independently chosen from an alkyl group comprising from 1 to 20 carbon atoms and an aryl group comprising from 6 to 30 carbon atoms; wherein at least one of substituents $R^1$ and $R^2$ comprises at least one electron withdrawing substituent chosen from F, Cl, Br, I, CN, NO$_2$, PO(OR)$_2$, OR, RCCO, SO, SO$_2$, SO$_2$R and wherein R in the at least one electron withdrawing substituent is chosen from an alkyl group or an aryl group; $R^3$ is chosen from a H atom, an alkyl group comprising from 1 to 20 carbon atoms, or an aryl group comprising from 6 to 12 carbon atoms, and n is a number ranging from 1 to 4. The term "alkyl group" as used herein describes a substituted or unsubstituted alkyl group having from 1 to 20, or from 1 to 12, or from 1 to 6 carbon atoms and may include linear, branched, or cyclic groups. Examples of suitable alkyl groups include, but are not limited to, methyl, ethyl, isopropyl, sec-butyl, tert-butyl, tert-amyl, n-pentyl, n-hexyl, cyclopropyl, cyclopentyl, and cyclohexyl. The term "aryl" group as used herein describes a substituted or unsubstituted aryl group having from 6 to 30 or from 6 to 12 or from 6 to 10 carbon atoms. Examples of aryl groups include, but are not limited to, phenyl, benzyl, tolyl, mesityl, and xylyl.

Further examples of aminosilanes with electron-withdrawing groups selected from Formula I are provided herein as Formula II:

$$A_n SiR^4_{4-n} \tag{II}$$

In Formula II, A is selected from the following amino groups (a) through (j), $R^4$ is chosen from hydrogen, an alkyl group comprising from 1 to 20 carbon atoms, or an aryl group comprising from 6 to 12 carbon atoms, and n is a number ranging from 1 to 4. The amino groups (a) through (j) are bonded to the Si atom as shown.

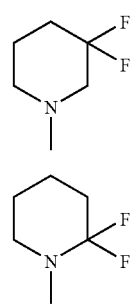

a b

-continued

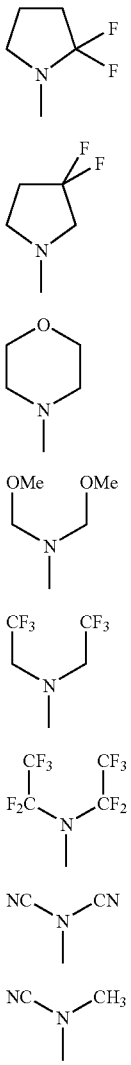

In certain embodiments, any one of, or all of $R^1$, $R^2$, $R$, $R^3$, $R^4$ and the at least one electron withdrawing substituent is substituted. In this or other embodiments, any one of, or all of $R^1$, $R^2$, $R$, $R^3$, $R^4$ and the at least one electron withdrawing substituent is substituted with a heteroatom such as, but not limited to, N, S, P, O. In other embodiments, any one of, or all of $R^1$, $R^2$, $R$, $R^3$, $R^4$ and the at least one electron withdrawing substituent is unsubstituted.

The term "electron withdrawing substituent" as used herein describes an atom or group thereof that acts to draw electrons away from the Si—N bond. Examples of suitable electron withdrawing substituents include, but are not limited to, halogens (F, Cl, Br, I), nitriles (CN), carboxylic acids (COOH), and carbonyls (CO). In certain embodiments, electron withdrawing substituent can be adjacent to or proximal to N in Formula I.

In certain embodiments, substituents $R^1$ and $R^2$ are linked in formula (I) to form a ring structure. In other embodiments, substituent $R^1$ and $R^2$ are not linked in formula (I).

While not being bound to theory, one of the requirements for silicon nitride precursors to be deposited at low temperatures (e.g., temperatures of 550° C. or below) may be to have Si—N bonds within the aminosilane precursor that are generally weaker than 90 kcal/mol to facilitate the deposition of Si—N on the substrate surface. This requires evaluating the Si—N bond energies of each precursor. However, rigorous bond energy calculations, based on the homolytic bond dissociation model, may fail to consistently characterize the qualitative relationship between the bond strengths and deposition temperature, which is expected to be roughly proportional due to the poor sensitivity of bond energies to deposition temperature. As an alternative to bond energy calculations, defined herein are Si—N formation energies that are used to quantify the relative strength of a Si—N bond in accordance with the following Equation (1):

$$(R^1R^2N)_n SiR^3_{4-n} + NH_3 \rightarrow (R^1R^2N)_{n-1} Si(NH_2) R^3_{4-n} + R^1R^2NH \quad (I)$$

In Equation (1) above, $R^1$ and $R^2$ are substituents of the commonly used precursors known in the art, which can be aminosilanes, β-aminoethylsilanes, cyclic silazanes, iminosilanes, bicyclosilazanes, hydrozinosilanes, pseudohalosilanes, and heterocyclic substituted silanes. The Si—N formation energies were calculated using Equation (1) on a chemical modeling software program entitled DMol³, Materials Studio v. 4.2.0.2., provided by Accelyrs, Inc. of San Diego, Calif. Applying Equation (1) and determining the formation energies using the modeling software, a strong Si—N bond would result in higher reaction energy and thus a higher deposition temperature (greater than 550° C.). To develop a aminosilane precursor that would deposit at a low processing temperature (e.g., 550° C. or less), one may want to weaken the Si—N bonds by removing electron density from the Si—N bonds by introducing electron withdrawing groups near the Si—N bond.

Using quantum mechanical density functional theory, extensive calculations were conducted using computer modeling software to systematically evaluate the reaction energies of various SiN precursors sequentially substituted with a variety of at least one electron withdrawing substituents. The calculations were done under the generalized gradient approximation (GGA) using the exchange-correlation functional proposed by Perdew-Wang (PW91) coupled with the double numerical atomic basis set augmented with polarization functions. All molecular structures were fully optimized to obtain the energetically most favorable geometries. Subsequently, the reaction energies were evaluated using the following equation (2):

$$\Delta E = -[E((R^1R^2N)_{n-1} Si(NH_2) R^3_{4-n}) + E(R^1R^2NH) - E(NH_3) - E((R^1R^2N)_n SiR^3_{4-n})] \quad (2)$$

In Equation (2), it is expected that the lower the ΔE value, the weaker the Si—N bonds and thus the lower the deposition temperatures can be achieved.

Figure 2:
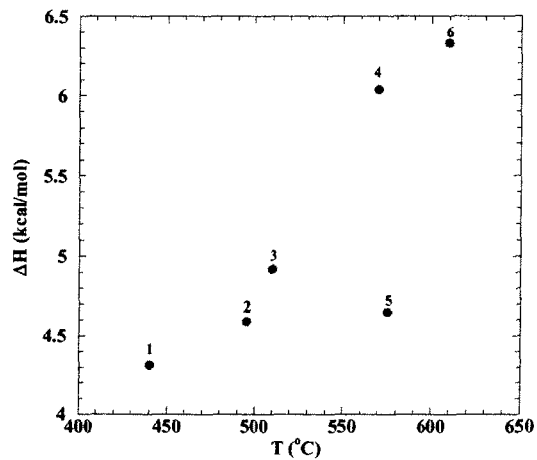
FIG. 2 provides a graphical representation of the correlation of experimentally measured deposition temperature and the calculated heat of reaction for aminosilane precursors 1 through 6 described herein.
Figure 3:
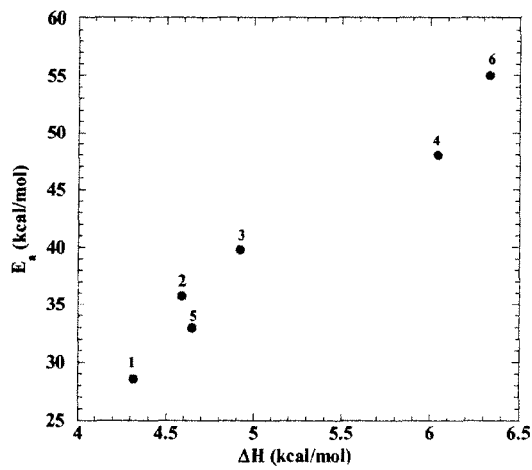
FIG. 3 provides a graphical representation of the correlation of experimentally measured deposition temperature and the calculated heat of reaction for aminosilane precursors 1 through 6 described herein.

FIG. 1 provides a graphical representation of the correlation of experimentally measured deposition temperature and calculated activation barrier levels using computer modeling software for certain aminosilane precursors 1 through 6 described below or tris(1,1-dimethylhydrazino)-tert-butylsilane, bis(1,1-dimethylhydrazino)ethylsilane, bis(1,1-dimethylhydrazino)methylsilane, bis(diethylamino)silane, tris(isopropylamino)silane, and tris(tert-butylamino)silane, respectively. FIG. 1 shows that the activation barrier increases with the deposition temperature. FIG. 2 provides a graphical representation of the experimentally measured deposition temperature and the calculated heat of reaction using computer modeling software for aminosilane precursors 1 through 6. FIG. 2 indicates that the deposition temperature increases with the heat of reaction. FIG. 3 provides a graphical representation of the correlation of the activation energy measured experimentally and the calculated heat of reaction using computer modeling software for aminosilane precursors 1 through 6. This example indicates that the activation barrier increases with the heat of reaction. By reviewing the results of FIGS. 1-3, in certain embodiments, the deposition temperature of a precursor can be computationally predicted by the heat of reaction through applying Equation (2) above. In certain embodiments, it is preferable that the activation energy of the aminosilane precursor is about 45 kcal/mol or below, or about 40 kcal/mol or below, or about 35 kcal/mol or below, or about 30 kcal/mol or below, or about 25 kcal/mol or below. In this or other embodiments, it is preferable that the reaction energy of the aminosilane precursor is about 5.5 kcal/mol or below, about 4.0 kcal/mol or below, about 3.5 kcal/mol or below, or about 3.0 kcal/mole or below, or about 2.5 kcal/mol or below.

The structures of the precursors 1 through 6, or tris(1,1-dimethylhydrazino)-tert-buylsilane, bis(1,1-dimethylhydrazine)ethylsilane, bis(1,1-dimethylhydrazino)methylsilane, bis(diethylamino)silane, tris(iso-propylamino)silane, and tris(tert-butylamino)silane, used in FIGS. 1 through 3, are shown below:

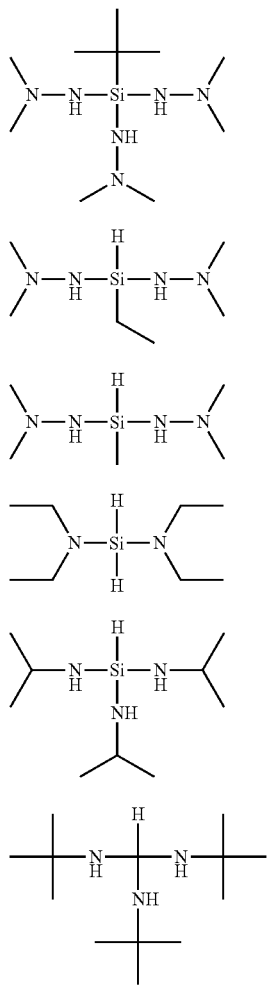

In one embodiment, the aminosilane precursors having at least one electron withdrawing substituent as described in formula (I) or (II) may be prepared by the amination reaction of chlorosilanes with corresponding amines. Representative amines well suited for the reaction are the alkyl, cyclic, and heterocyclic. Preferred amines are the lower alkyl amines, e.g., ethyl, iso-propyl, t-butyl, and cyclohexyl. Further the amines may be primary or secondary depending upon the product desired. The animation reactions are typically conducted at room temperature or below. Hydrocarbon solvents, such as hexane and pentane, are usually used as reaction media. In one particular embodiment, aminosilane precursors having formula (I) or (II) may be made as illustrated by the following exemplary reactions (A), (B), and (C).

$$R^1R^2NH + ClSiH_3 \rightarrow R^1R^2N\text{---}SiH_3 + R^1R^2NH\text{---}HCl \quad (A)$$

$$4R^1R^2NH + H_2SiCl_2 \rightarrow R^1R^2N\text{---}SiH_2\text{---}NR^1R^2 + 2R^1R^2NH\text{---}HCl \quad (B)$$

$$6R^1R^2NH + HSiCl_3 \rightarrow (R^1R^2N)_3SiH + 3R^1R^2NH\text{---}HCl \quad (C)$$

In another embodiment, aminosilane precursors of formula (I) are made using the following method that is described herein in Examples 4, 5, and 6. In these or other embodiments, the aminosilane precursors described herein made be prepared by the transamination reaction from more commonly available aminosilanes.

As mentioned previously, the aminosilane precursor of formula (I) or (II) described herein may be used as precursor for the deposition of a silicon-containing film, such as but not limited to, silicon nitride, silicon oxide, silicon carbo-nitride, and silicon oxynitride films, onto a substrate. Examples of suitable substrates include but are not limited to, semiconductor materials such as gallium arsenide ("GaAs"), boronitride ("BN") silicon, and compositions containing silicon such as crystalline silicon, polysilicon, amorphous silicon, epitaxial silicon, silicon dioxide ("SiO$_2$"), silicon carbide ("SiC"), silicon oxycarbide ("SiOC"), silicon nitride ("SiN"), silicon carbonitride ("SiCN"), organosilicate glasses ("OSG"), organofluorosilicate glasses ("OFSG"), fluorosilicate glasses ("FSG"), and other appropriate substrates or mixtures thereof. Substrates may further comprise a variety of layers to which the film is applied thereto such as, for example, antireflective coatings, photoresists, organic polymers, porous organic and inorganic materials, metals such as copper and aluminum, or diffusion barrier layers. The aminosilane precursor of formula (I) may be deposited using any of the techniques described herein or known in the art. Exemplary deposition techniques include, but are not limited to, chemical vapor deposition (CVD), atomic layer deposition (ALD), pulsed CVD, plasma-assisted chemical vapor deposition (PACVD), and plasma-enhanced chemical vapor deposition (PECVD).

In certain embodiments, the aminosilane precursors are deposited onto a substrate using a CVD or ALD technique. In certain embodiments, the deposition of the aminosilane precursor of formula (I) or (II) may be conducted at temperatures of 550° C. or below, or 500° C. or below, or 400° C. or below, 300° C. or below or 200° C. or below, or 100° C. or below, or any ranges from the foregoing end-points such as, for example, 300° C. to 550° C. Depending upon the deposition technique used, pressures of from 50 mtorr to 100 torr are exemplary. In a typical CVD deposition process, the aminosilane precursor is introduced into a process chamber such as a vacuum chamber. In certain embodiments, other chemical reagents, besides the aminosilane precursor of formula (I), may be introduced before, during, and/or after the introduction of the aminosilane precursor. An energy source, such as, for example, thermal, plasma or other source, energizes the aminosilane precursor and optional chemical reagents thereby forming a film on at least a portion of the substrate.

Atomic layer deposition (ALD) comprises the sequential introduction of pulses of a first precursor and, in certain embodiments, a second precursor. In embodiments wherein more than one precursor is used in the ALD process, there is the sequential introduction of a pulse of a first precursor, followed by a pulse of a purge gas and/or a pump evacuation, followed by a pulse of a second precursor, which is followed by a pulse of a purge gas and/or a pump evacuation. Sequential introduction of separate pulses results in alternating self-limiting chemisorption of mono-layers of each precursor on the surface of the substrate and forms a monolayer of the deposited materials for each cycle. The cycle is repeated as necessary to generate a film of desired thickness. During ALD processing, the substrate is kept at a temperature range that facilitates chemisorption, i.e., is low enough to maintain intact bonds between adsorbed species and the underlying substrate yet high enough to avoid condensation of the precursors and to provide sufficient activation energy for the desired surface reactions in each process cycle. The process chamber temperature may range from 0° C. to 400° C., or from 0° C. to 300° C., or from 0° C. to 275° C. The pressure within the process chamber during ALD processing may range from 0.1 to 1000 Torr, of from 0.1 to 15 Torr, or from 0.1 to 10 Torr. It is understood, however, that the temperature and pressure for any particular ALD process may vary depending upon the one or more precursors involved.

The growth rate of ALD is low compared to conventional CVD process. A typical growth rate of an ALD process is 1-2 Å/cycle. One approach to increase of growth rate is by conducting the deposition at a higher substrate temperature. The aminosilane precursors described herein can deposit silicon containing film at relatively lower temperature, and therefore increase the film growth rate.

Depending upon the desired film, conventional oxidizing agents may be used in the deposition process of the silicon-containing films. Representative oxidizing agents include hydrogen peroxide, nitrous oxide, ozone, and molecular oxygen. Typically, the oxidizing agent to aminosilane precursor ratio is greater than 0.1, preferably from 0.1 to 6 moles oxidizing agent per mole of organoaminosilane precursor.

The deposition of the aminosilane precursors of formula (I) or (II) may be carried out in the absence of, or in the presence of, an active nitrogen source such as ammonia, hydrazine, alkylhydrazine, dialkylhydrazine and mixtures thereof. Molar ratios of the nitrogen source to aminosilane generally are broadly within the range of from 0: to >10:1. The upper limit is restricted by the dilution effect on the precursor and the dilution effect will significantly diminish the deposition rate. Preferred ranges are from 0.1 to 4:1. The formation of films via deposition may also be carried out with or without other gases including with inert gases, such as nitrogen and helium. The use of gases by the fabricator to achieve corresponding dilution of the precursor may improve the conformality of the deposition or improve the penetration for chemical vapor infiltration.

As mentioned previously, in certain embodiments, additional chemical reagents or precursors may be introduced before, during, and/or after the introduction of the aminosilane precursor of formula (I) or (II) into the process chamber. The choice of chemical reagent may depend upon the composition of the desired resultant films. Exemplary chemical reagents include, but are not limited to oxidants (i.e., $O_2$, NO, $NO_2$, $O_3$, CO, $CO_2$, etc.); water; halides; halogen-containing silanes; alkylchlorosilanes, alkylbromosilanes, or alkyliodosilanes; silicon halide complexes such as silicon tetrachloride, silicon tetrabromide, or silicon tetraiodide; or combinations thereof. It is also envisioned that derivatives of the above complexes may also be used. The chemical reagents may be delivered directly as a gas to the process chamber, delivered as a vaporized liquid, a sublimed solid and/or transported by an inert carrier gas into the reaction chamber. Examples of inert carrier gases include nitrogen, hydrogen, argon, xenon, etc.

In carrying out deposition processes, the aminosilanes described herein can be blended with other silyl precursors to alter film properties. Examples of other precursors include bis-tert-butylaminosilane, tris-iso-propylaminosilane, bis-diethylaminosilane, tris-dimethylaminosilane, and bis-iso-propylaminosilane.

Any of the aforementioned film formation methods described herein, as well as other film formation methods known in the art, may be used alone or in combination.

The following examples illustrate the aminosilane precursors described herein are not intended to limit it in any way.

EXAMPLES

Example 1

The Effect of —$CH_3$ Displacement by —$CF_3$ in BTBAS

One of the methyl groups in the t-butyl groups of bis(tert-butylamino)silane BTBAS was sequentially displaced with the —$CF_3$ group as shown in structure 7 below.

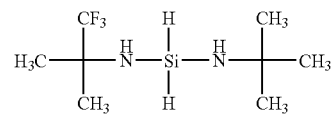

7

Figure 4:
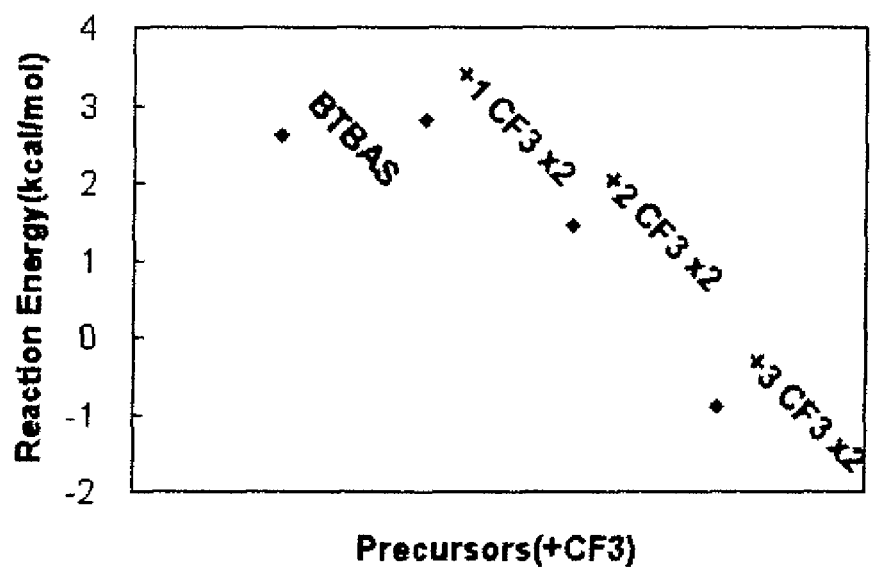
FIG. 4 provides a graphical representation of the calculated reaction energy expressed in kilocalories per mole (kcal/mol) for the aminosilane precursor bis(tertiarybutylamino)silane and for aminosilane precursors having one, two, or three methyl groups within the bis(tertiarybutylamino)silane precursor replaced with the at least one electron withdrawing group CF$_3$ as described in Example 1.

The reaction energy for the above molecule and for similar molecules having 2 or 3 methyl groups displaced was determined using Equation (2) described above a chemical modeling software program entitled DMol$^3$, Materials Studio v. 4.2.0.2., provided by Accelrys, Inc. of San Diego, Calif. and the results are presented in FIG. 4. FIG. 4 shows that the full displacement of methyl groups for the —$CF_3$ groups results in a decrease of reaction energies. In particular, full displacement of all of the methyl groups in the molecule by the —$CF_3$ groups changes the reaction from endothermic to exothermic. Thus, the split of the Si—N bonds is expected to occur at a much lower temperature than in BTBAS thereby allowing a lower deposition temperature.

Example 2

The effect of —$CH_3$ Displacement by —CN in BTBAS

Figure 5:
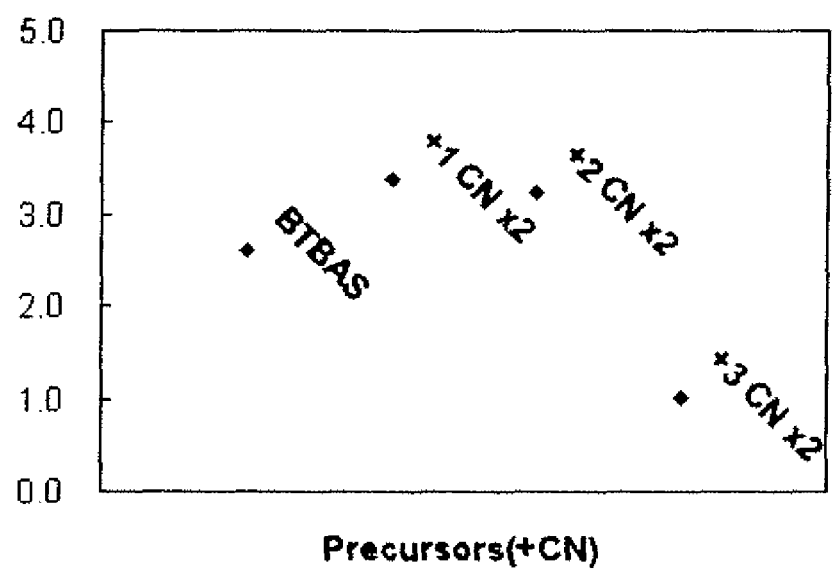
FIG. 5 provides a graphical representation of the calculated reaction energy expressed in kcal/mol for the aminosilane precursor bis(tertiarybutylamino)silane and for aminosilane precursors having one, two, or three methyl groups within the bis(tertiarybutylamino)silane precursor replaced with the at least one electron withdrawing group CN as described in Example 2.

The methyl groups in the t-butyl groups of BTBAS were sequentially displaced with the —CN groups. The reaction energy for BTBAS and for aminosilane precursors of formula (1) having 1, 2, or 3 methyl groups displaced with —CN groups was determined using Equation (2) described above and a chemical modeling software program entitled DMol$^3$, Materials Studio v. 4.2.0.2., provided by Accelrys, Inc. of San Diego, Calif. The results are presented in FIG. 5. The displacement initially results in increase of reaction energies due to the formation of intramolecular hydrogen bonding. However, upon full displacement, the reaction energy is lower than for BTBAS by about 1.6 kcal/mol. Thus the split of the Si—N bonds is expected to occur at a lower temperature than in BTBAS.

Example 3

The Effect of —F Substitution

A series of aminosilane precursors having alkyl and aryl groups comprising at least one electron withdrawing substituent or fluorine were compared against similar aminosilane precursors that did not contain fluorine but rather hydrogen. Calculations were performed to examine displacement of H by F for the molecules listed in Table 1, where the calculated heats of reaction are also shown using Equation (2) described herein and a chemical modeling software program entitled DMol$^3$, Materials Studio v. 4.2.0.2., provided by Accelrys, Inc. of San Diego, Calif. The results of the comparison are provided in Table I below.

TABLE I

| Example | Molecule | ΔH (kcal/mol) |
|---|---|---|
| Comparative Example 1 | (CH$_3$CH$_2$)$_2$N—SiH$_3$ (diethylamino silane) | 1.19 |
| Example 3a | (FH$_2$C-CH$_2$)(FH$_2$C-CH$_2$)N—SiH$_3$ | −0.338 |
| Comparative Example 2 | pyrrolidino-SiH$_3$ | 1.26 |
| Example 3b | α-FHC pyrrolidino-SiH$_3$ | 0.93 |
| Example 3c | α-F$_2$C pyrrolidino-SiH$_3$ | 0.42 |
| Comparative Example 3 | piperidino-SiH$_3$ | 0.27 |
| Example 3d | γ-FHC piperidino-SiH$_3$ | 0.07 |
| Example 3e | β-FHC piperidino-SiH$_3$ | 0.11 |
| Example 3f | α,α′-di-FHC piperidino-SiH$_3$ | −1.20 |

The results indicate that in all cases the reaction energies can be lowered by the displacement of H by F. In particular, the temperature reduction effect is more pronounced at the α-site followed by the β-site and then γ-site. Higher displacement yields more favorable reaction energies.

Example 4a

Preparation of 3,3-difluoropiperidine Precursor to bis(3,3-difluoropiperidine)silane A 240 mL teflon reactor equipped with a magnetic stirring bar, N$_2$ purge valve and rubber septum was charged with a solution of N-t-butyl-3-piperidone (25 g, 0.1255 mol) in CH$_2$Cl$_2$ (50 mL) and cooled to 0° C. To this solution, bis(2-methoxyethyl)amino sulfur trifluoride (41.58 g,0.1882 mol) was added. The mixture was then brought to room temperature and stirred for 16 hours. The mixture was poured into a 250 mL glass flask and treated with 25 milliliters (mL) of ice-water at 1° C. The organic phase was separated in a separatory funnel. The organic solution was made basic using 15% aqueous NaOH and then dried (MgSO$_4$), filtered and evaporated in-vacuo. The residue was combined with 3M HCl in 250 mL round bottom flask equipped with a magnetic stirring bar and nitrogen inlet tube and heated at 60° C. for 90 minutes. The mixture was neutralized with 15% aqueous NaOH, extracted into diethyl ether, separated from the aqueous phase, dried (MgSO$_4$); filtered and then evaporated in-vacuo. The pure product or 3,3-difluoropiperidine was obtained by distillation at 40° C. (0.1 Torr) and analyzed by G.C.M.S. Mass spectrum.

Example 4b

Preparation of bis(3,3-difluoropiperidino)silane by Transanimation Reaction

A quantity of 0.1 mol 3,3-difluoropiperidine and 0.1 mol bis(t-butylamino)silane were mixed and stirred in a flask under the protection of nitrogen. Every 4 hours, the mixture was pumped with vacuum of 100 torr for 30 minutes. After 48 hours, the end-product bis(3,3-difluoropiperidino)silane was obtained by vacuum distillation at 118° C. / 10 torr.

Example 5

Preparation of bis[bis(2-methoxyethyl)amino]silane by Transanimation Reaction

A quantity of 0.1 mol bis(2-methoxyethyl)amine and 0.1 mol bis(t-butylamino)silane were mixed and stirred in a flask under the protection of nitrogen. Every 4 hours, the mixture was pumped with vacuum at 100 torr for 30 minutes. After 48 hours, the product bis[bis(2-methoxyethyl)amino]silane was obtained by vacuum distillation at 54° C./10 torr.

Example 6

Preparation of bis(2-methoxyethyl)aminosilane by Transanimation Reaction

A quantity of 0.1 mol bis(2-methoxyethyl)amine and 0.1 mol diethylaminosilane were mixed and stirred in a flask under the protection of nitrogen. Every 4 hours, the mixture was pumped with vacuum at 100 torr for 30 minutes. After 48 hours, the product bis(2-methoxyethyl)amino]silane was obtained by vacuum distillation at 40° C. / 10 torr.

The invention claimed is:
1. An aminosilane precursor for depositing silicon-containing film comprising the following formula (I):

$$(R^1R^2N)_n SiR^3{}_{4-n} \quad (I)$$

wherein substituents $R^1$ and $R^2$ are each independently chosen from an alkyl group comprising from 1 to 20 carbon atoms and an aryl group comprising from 6 to 30 carbon atoms, wherein $R^1$ and $R^2$ in formula (I) are selected from the group consisting of $R^1$ and $R^2$ linked to form a ring structure or $R^1$ and $R^2$ not linked to form a ring structure, wherein at least one of substituents $R^1$ and $R^2$ comprises at least one electron withdrawing substituent chosen from F, Cl, Br, I, CN, $NO_2$, $PO(OR)_2$, OR, RCOO, SO, $SO_2$, $SO_2R$ and wherein R in the at least one electron withdrawing substituent is chosen from an alkyl group or an aryl group;

$R^3$ is chosen from H, an alkyl group comprising from 1 to 20 carbon atoms, or an aryl group comprising from 6 to 12 carbon atoms, wherein any one or all of $R^1$, $R^2$, R, $R^3$ and the electron withdrawing substituent is substituted or unsubstituted, and n is a number ranging from 1 to 4.

2. The aminosilane precursor of claim 1 wherein $R^1$ and $R^2$ are linked to form a ring structure and at least one of $R^1$ and $R^2$ is substituted.

3. The aminosilane precursor of claim 1 comprising bis(3,3-difluoropiperidino)silane.

4. A process for depositing a silicon-containing film on a substrate via chemical vapor deposition, the process comprising:
   providing the substrate in a process chamber;
   introducing an aminosilane precursor into the process chamber at a temperature and a pressure sufficient to react and deposit the silicon-containing film on the substrate wherein the aminosilane precursor comprises a compound having the following formula (I):

$(R^1R^2N)_n SiR^3_{4-n}$ (I)

wherein substituents $R^1$ and $R^2$ are each independently chosen from an alkyl group comprising from 1 to 20 carbon atoms and an aryl group comprising from 6 to 30 carbon atoms,
   wherein at least one of substituents $R^1$ and $R^2$ comprises at least one electron withdrawing substituent chosen from F, Cl, Br, I, CN, $NO_2$, $PO(OR)_2$, OR, RCOO, SO, $SO_2$, $SO_2R$ and wherein R in the at least one electron withdrawing substituent is chosen from an alkyl group or an aryl group, and $R^3$ is chosen from H, an alkyl group comprising from 1 to 20 carbon atoms, or an aryl group comprising from 6 to 12 carbon atoms, and n is a number ranging from 1 to 4.

5. The process of claim 4 wherein the introducing step further comprises a nitrogen source chosen from ammonia, nitrogen and hydrazine.

6. The process of claim 5 wherein the nitrogen source is ammonia or nitrogen and the nitrogen source is present in a nitrogen source: precursor range of from 0.1 to 4:1.

7. The process of claim 4 wherein the temperature ranges from about 400° C. to about 700° C.

8. The process of claim 4 wherein the pressure ranges from about 20 mTorr to about 20 Torr.

9. An aminosilane precursor for depositing silicon-containing film comprising the following formula (II):

$A_n SiR^4_{4-n}$ (II)

wherein when A is at least one group chosen from the following amino groups (a) through (d) and (f) through (h), $R^4$ is chosen from hydrogen, an alkyl group comprising from 1 to 20 carbon atoms, or an aryl group comprising from 6 to 12 carbon atoms, and n is a number ranging from 1 to 4, and when A is (i), $R^4$ is chosen from hydrogen, an alkyl group comprising from 1 to 20 carbon atoms, or an aryl group comprising from 6 to 12 carbon atoms, and n is a number ranging from 3 to 4, and when A is (j), $R^4$ is chosen from hydrogen, an alkyl group comprising from 1 to 20 carbon atoms, or an aryl group comprising from 6 to 12 carbon atoms, and n is a number ranging from 2 to 4.

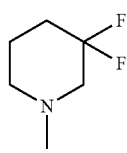

a

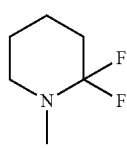

b

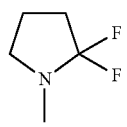

c

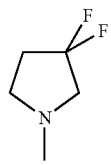

d

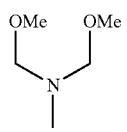

f

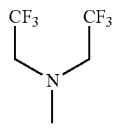

g

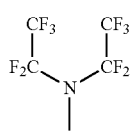

h

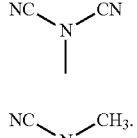

i

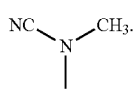

j

10. The aminosilane precursor of claim 9 wherein A is the following amino group (a):

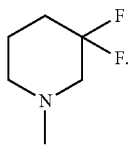

a

11. The aminosilane precursor of claim 9 wherein A is the following amino group (b):

b

12. The aminosilane precursor of claim 9 wherein A is the following amino group (c):

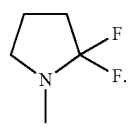

c

13. The aminosilane precursor of claim 9 wherein A is the following amino group (d):

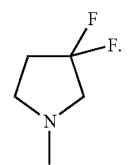

d

14. The aminosilane precursor of claim 9 wherein A is the following amino group (f):

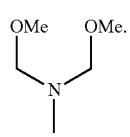

f

15. The aminosilane precursor of claim 9 wherein A is the following amino group (g):

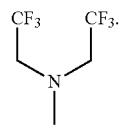

g

16. The aminosilane precursor of claim 9 wherein A is the following amino group (h):

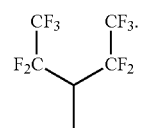

h

17. The aminosilane precursor of claim 9 wherein A is the following amino group (i):

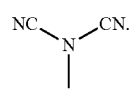

i.

18. The aminosilane precursor of claim 9 wherein A is the following amino group (j):

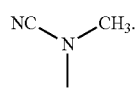

j

19. The aminosilane precursor of claim 1 wherein $R^1$ and $R^2$ are not linked to form a ring structure.

20. A aminosilane precursor comprising bis[bis(2-methoxyethyl)amino]silane.

21. A aminosilane precursor comprising bis(2-methoxyethyl)aminosilane.

* * * * *

UNITED STATES PATENT AND TRADEMARK OFFICE
CERTIFICATE OF CORRECTION

PATENT NO. : 8,129,555 B2
APPLICATION NO. : 12/190125
DATED : March 6, 2012
INVENTOR(S) : Hansong Cheng et al.

Page 1 of 1

It is certified that error appears in the above-identified patent and that said Letters Patent is hereby corrected as shown below:

In the Claims

Column 18, Line 20

In Claim 16 delete " 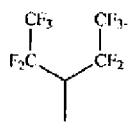 " and insert -- 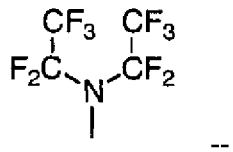 --

Signed and Sealed this
Twenty-third Day of April, 2013

Teresa Stanek Rea
*Acting Director of the United States Patent and Trademark Office*